United States Patent
Emerson et al.

(10) Patent No.: US 9,474,462 B2
(45) Date of Patent: Oct. 25, 2016

(54) SYSTEMS AND METHODS FOR DYNAMIC ADJUSTABLE SPATIAL GRANULARITY FOR EEG DISPLAY

(71) Applicant: The Trustees of Columbia University in the City of New York, New York, NY (US)

(72) Inventors: Ronald G Emerson, Chappaqua, NY (US); Catherine A. Schevon, New York, NY (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 699 days.

(21) Appl. No.: 13/728,496

(22) Filed: Dec. 27, 2012

(65) Prior Publication Data

US 2013/0116590 A1    May 9, 2013

Related U.S. Application Data

(63) Continuation of application No. PCT/US2011/042663, filed on Jun. 30, 2011.

(60) Provisional application No. 61/361,171, filed on Jul. 2, 2010.

(51) Int. Cl.
  A61B 5/00    (2006.01)
  A61B 5/04    (2006.01)
  A61B 5/0476  (2006.01)

(52) U.S. Cl.
  CPC ......... *A61B 5/0476* (2013.01); *A61B 5/04012* (2013.01); *A61B 5/7278* (2013.01); *A61B 5/742* (2013.01)

(58) Field of Classification Search
  CPC .. A61B 5/0476; A61B 5/7278; A61B 5/742; A61B 5/04012
  See application file for complete search history.

(56) References Cited

U.S. PATENT DOCUMENTS

| 4,610,259 A | 9/1986 | Cohen et al. |
| 6,353,754 B1* | 3/2002 | Fischell et al. ............... 600/544 |
| 6,687,525 B2* | 2/2004 | Llinas et al. .................. 600/407 |
| 2004/0122335 A1* | 6/2004 | Sackellares et al. ......... 600/544 |
| 2009/0094305 A1* | 4/2009 | Johnson ....................... 708/403 |

FOREIGN PATENT DOCUMENTS

| WO | WO 2009/063446 | 5/2009 |
| WO | WO 2009/069134 | 6/2009 |
| WO | WO 2010/065678 | 6/2010 |

OTHER PUBLICATIONS

Holmes, et al., "Comparing noninvasive Dense Array and intracranial Electroencephalography for Localization of Seizures", *Neurosurgery*, 66(2):354-362 (2010).

Schevon, et al., "Inadequacy of Standard Screen Resolution for Localization of Seizure Recorded from Intracranial Electrodes", *Epilepsia*, 45(11):1453-1458 (2004).

International Search Report and Written Opinion for PCT/US2011/042663, dated Nov. 15, 2011 (corresponds to U.S. Appl. No. 13/728,496).

* cited by examiner

*Primary Examiner* — Christine H Matthews
*Assistant Examiner* — Joshua D Lannu
(74) *Attorney, Agent, or Firm* — Baker Botts L.L.P.

(57) ABSTRACT

A method for organizing and displaying EEG data obtained from C EEG channels on a computer system in a user-friendly manner includes placing the C EEG channels into a schematic placement diagram dividing the C EEG channels, using a processor, into G channel groups for each of the G channel groups, combining any of the C EEG channels in such G channel group, using a processor, into a single trace, and for each of the G channel groups, displaying the single trace. A system for organizing and displaying EEG data is also provided.

28 Claims, 8 Drawing Sheets

SYSTEMS AND METHODS FOR DYNAMIC ADJUSTABLE SPATIAL GRANULARITY FOR EEG DISPLAY

CROSS-REFERENCE TO RELATED APPLICATIONS

This application is a continuation of International Patent Application Ser. No. PCT/US2011/042663, filed Jun. 30, 2011, and claims priority to U.S. Provisional Patent Application Ser. No. 61/361,171, filed on Jul. 2, 2010, the contents of both of which are hereby incorporated herein by reference in their entireties.

BACKGROUND

1. Field

The present application relates to systems and methods for dynamically configurable, assisted visual review of EEG signal traces.

2. Background Art

EEG can be interpreted by visually reviewing tracings of the time domain signal recorded from sensors placed on the scalp, inside the cranium, or inside the brain parenchyma. The interpretation can be informed not only by the signals observed, but also by the spatial location and arrangement of the sensors from which the signals are recorded. For example, during intracranial recording, arrays of disk electrodes arranged in an 8×8 grid and regularly spaced 1 cm apart can be placed on the brain surface under the dura. The resulting EEG can be viewed as a linear sequence of traces, one per electrode, ordered in a way that corresponds to the physical arrangement of the recording sensors (e.g. by row and column).

As the number of sensors grows, viewing the traces in this way can become ever more cumbersome. It can be difficult to spot important abnormalities when the reader is faced with, for example, more than 100 traces on a single screen. In addition to the number of traces, the increasingly complex physical layout can also greatly increase the difficulty of interpreting the recording.

An EEG sensor array can be arranged in 3 dimensions, including for example sensors penetrating into the brain parenchyma. As such, EEG can be viewed as a 4-dimensional construct with 3 spatial and one temporal axes. The granularity along each axis can vary according to clinical needs and the types of sensors used. One known practice of presenting EEG data in the format of voltage/time plots, essentially one per channel, can be impractical for viewing data from large numbers of sensors in complex physical arrangements. Accordingly, there exists a need for an improved technique for distilling useful clinical information from large numbers of sensors.

SUMMARY

Systems and methods for display of EEG data are provided herein. In some embodiments, a method for organizing and displaying EEG data obtained from C EEG channels on a computer system in a user-friendly manner includes placing the C EEG channels into a schematic placement diagram, dividing the C EEG channels, using a processor, into G channel groups, for each of the G channel groups, combining any of the C EEG channels in such G channel group, using a processor, into a single trace, and for each of the G channel groups, displaying the single trace.

In some embodiments, the method also includes selecting a plurality of the G channel groups for zooming out. The method can include merging the selected plurality of G channel groups into a new single trace.

In some embodiments, the method also includes selecting one of the G channel groups for zooming in. The method can include dividing the selected G channel group into a plurality of composite channels.

In some embodiments, the method also includes displaying a montage. The method can include saving settings for later use or sharing.

In some embodiments, the method also includes computing a specific feature from the C EEG channels. The method can include mapping the specific feature to a current set of the G channel groups. Mapping the specific feature can include summing a number of detections of the specific feature for a predetermined time slice within each G channel group. The method can also include encoding the feature into the EEG display. The specific feature can be a high-frequency oscillation, and the specific feature can be coherence. Encoding the feature into the EEG display can include changing a color of an EEG trace using a color spectrum.

Throughout the drawings, the same reference numerals and characters, unless otherwise stated, are used to denote like features, elements, components or portions of the illustrated embodiments. Moreover, while the disclosed subject matter will now be described in detail with reference to the Figs., it is done so in connection with the illustrative embodiments.

DETAILED DESCRIPTION

One aspect of the disclosed subject matter relates to a zoom feature for EEG viewing. According to the disclosed subject matter, the EEG view can be dynamically warped in any dimension in a way that is directly controllable and that preserves the fundamental nature of the EEG data. In addition, features can be extracted from the raw data and added to the display in a way that places them in their temporo-spatial context.

Figure 1:
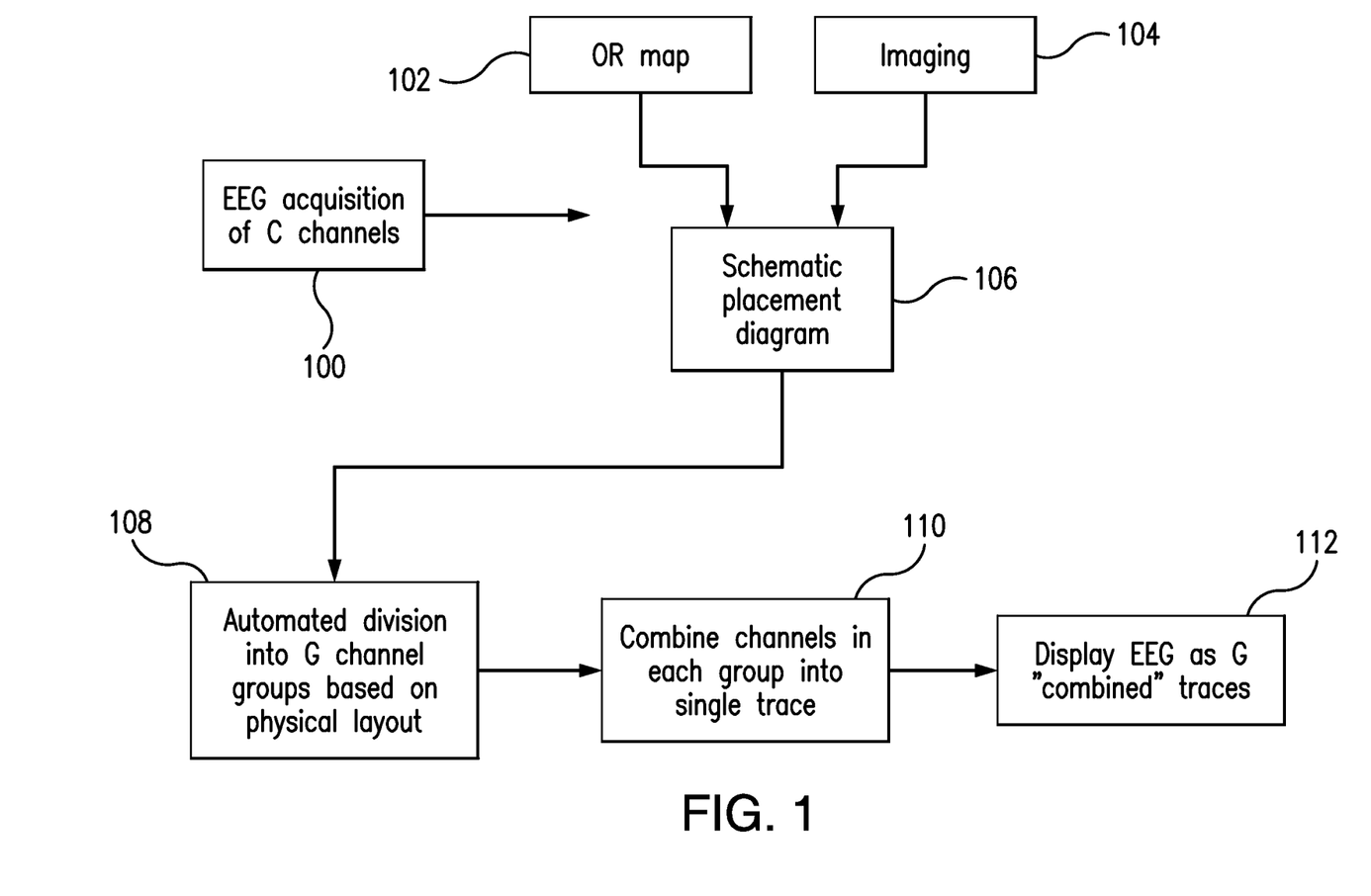
FIG. 1 is a diagram illustrating a method implemented in accordance with some embodiments of the disclosed subject matter.

FIG. 1 is diagram showing an exemplary method according to the disclosed subject matter. At 100, acquisition of EEG channels occurs. A number, C, of EEG channels of raw EEG data are acquired. At 102, OR mapping occurs, and at 104, imaging is performed. The result of the OR mapping 102 and imaging 104 can be combined to create a schematic placement diagram at 106. At 108, the EEG channels can be divided into G channel groups. The G channel groups can be determined based on physical layout, and the number of G channel groups can be less than or equal to the number of C EEG channels. At 110, channels in each G channel group can be combined into a single trace. At 112, the EEG data is displayed as G "combined" traces.

Figure 8:
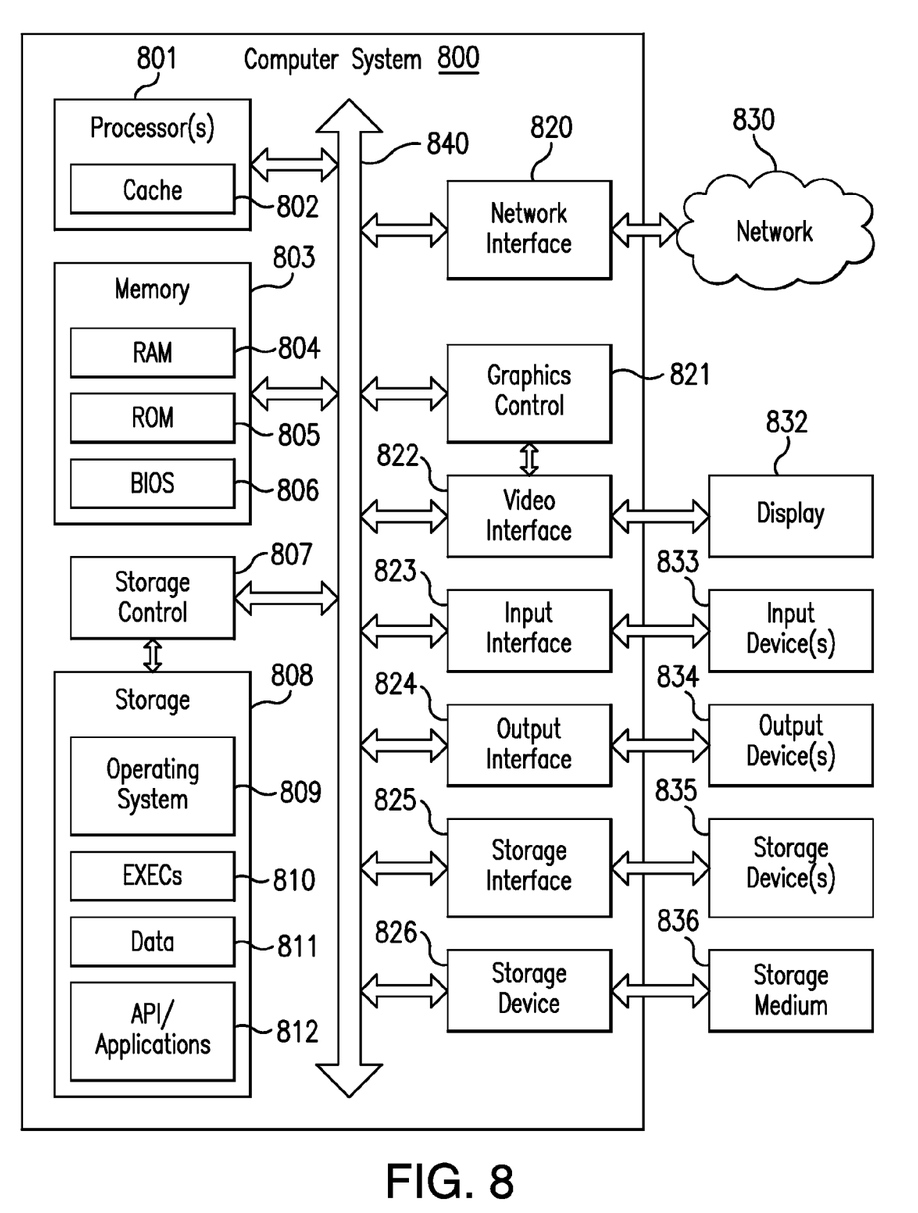
FIG. 8 is a block diagram illustrating a system in accordance with some embodiments of the disclosed subject matter.

The components of FIG. 1 can be software modules running on a computer, a processor, or a network of interconnected processors and/or computers that communicate through TCP, UDP, or any other suitable protocol, for example, as shown in FIG. 8. Conveniently, each module is software implemented and stored in random access memory of a suitable computer, e.g., a workstation computer. The software can be in the form of executable object code, obtained, e.g., by compiling from source code. Source code interpretation is not precluded. Source code can be in the form of sequence-controlled instructions as in Fortran, Pascal or "C," for example.

The disclosed subject matter can permit viewing of a large number of recorded signals by combining groups of channels into a single trace in a way that can be user-modifiable and can preserve temporal resolution and frequency content. In an exemplary embodiment, a 16-channel microgrid can be viewed as a single trace obtained by averaging the signals together. The composite signal appears as an EEG trace, which can be interpreted in the usual manner, and contains the information from each of the individual channels. Depending on requirements for clinical interpretation, this channel can be "zoomed in" to show the individual 16 traces, or it can be further combined with other nearby electrodes ("zooming out"). The zoom can operate non-uniformly, with varied degrees of zooming being applied concurrently to different brain areas.

Figure 2:
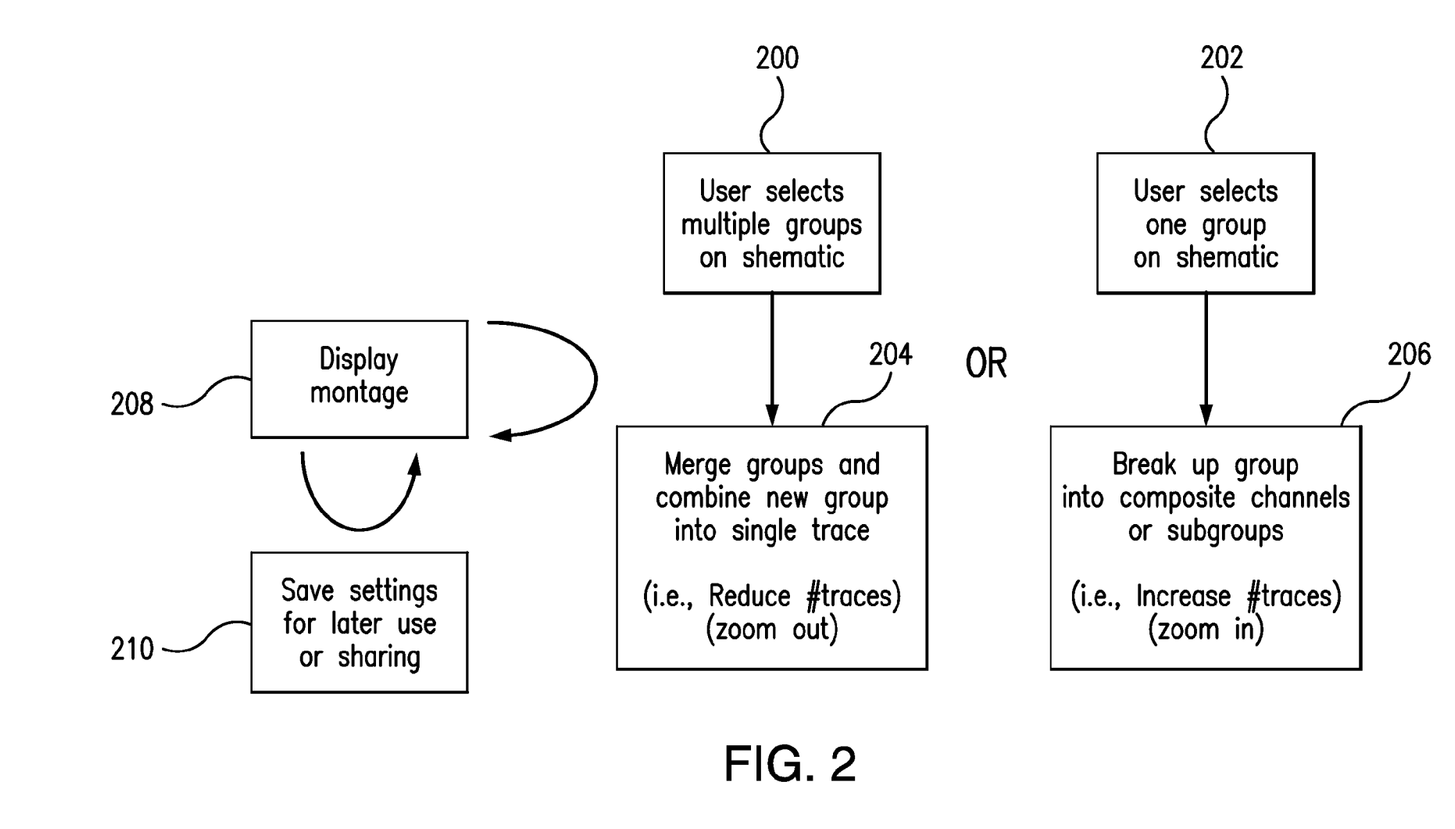
FIG. 2 is a diagram illustrating further details of the method of FIG. 1.

Referring to FIG. 2, an exemplary arrangement of user modification will be described. At 200, a user selects multiple groups on a schematic. In response, at 204, the groups are merged and new groups are combined into a single trace. Accordingly, the number of traces are reduced, performing a "zoom out." Alternatively, at 202, a user selects one group on a schematic. In response, at 206, the group is broken up into composite channels or subgroups. Accordingly, the number of traces is increased, performing a "zoom in." The zooming in or zooming out is a function that can be applied to a specific location or set of traces. As an additional feature, at 208, the user can display a montage, which will be described in further detail below. At 210, the user can save settings for later use or sharing.

Figure 3:
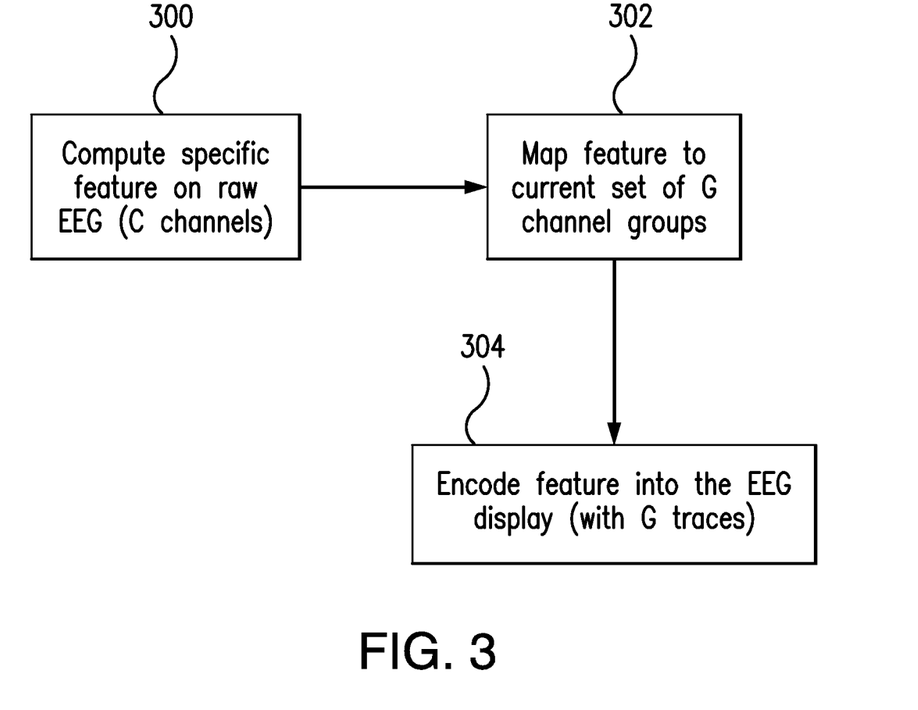
FIG. 3 is a diagram illustrating further details of the method of FIG. 1.

Referring to FIG. 3, an exemplary arrangement of feature display will be described. At 300, at least one specific feature of the C EEG channels of raw data is computed. At 302, the feature is mapped to the current set of G channel groups. At 304, the feature is encoded into the EEG display of the G traces.

Where rapid visual review of chronically recorded data in a clinical setting is necessary, for practical purposes, the time allotted to review of EEG data can be limited to 30 minutes, preferably less. An expert reviewer can scroll through the recordings at 10-20 times the speed of real time and identify departures from the usual background pattern. However, this task can become more difficult as the number of channels increases, and for screening purposes, some reviewers can limit the view to 40-50 channels. For example, an implantation with 256 channels distributed uniformly over a large area of neocortex and deep regions can be used. Using a 256 channel recording, a reviewer can laboriously select channels from the set and create a screening montage. This can cause the reviewer to miss information that resides only on the omitted channels.

According to the disclosed subject matter, in an exemplary embodiment, a user can start with a subset of channels, for example 64 channels, derived from an original set of, for example, 256 channels, by dividing the original set of channels into a subset of spatially contiguous sets, then averaging the channels in each subset to produce a single composite signal corresponding to that set. After inspecting this set carefully for a few pages, the user can elect to reduce the number of traces further by choosing inactive regions to merge adjacent channel sets. Thus, spatial resolution can be higher in the areas of interest and lower in the areas that are less active, but instead of eliminating channels in the less active areas, channels can be combined so that no information is lost.

According to another aspect of the disclosed subject matter, a reviewer can change the zoom feature dynamically in response to electrophysiological changes noted on review. For example, the reviewer can detect a seizure and stop the review to take a closer look. The reviewer can then zoom in on the channels active during the seizure, splitting the channel sets apart and increasing the number of traces viewed. To compensate for the larger number of viewed traces in the focus area, grouping can be increased in areas of less interest to reduce the number of traces back to a manageable level. Thus, rather than eliminating channels entirely from view, all of the data can be represented on the screen. Subsequently, the reviewer can return to the previous settings (for example, to a screening montage) and continue with the review process.

Channels can be identified, and implicitly located, according to their location within an array. In an exemplary embodiment, a silastic sheet with embedded electrodes having strip or grid geometry can be used, and a representation of the corresponding arrays with name labels can be used. For example, two 8×8 electrode grids, GA and GB, can be placed on different brain areas. The electrodes, or channels, in each grid can be numbered 1-64, with a first row having electrodes 1-8, a second row having electrodes 9-16, etc. A name for each channel can be derived from the grid name and the channel number in each grid (for example, channel GA15 can represent electrode 15 in grid GA). Additionally, neuroimaging can be used to map the electrode grids, or grid space, onto physical brain locations.

For grouping purposes, a user can reduce the number of channels in a grid, for example by reducing grid GA to 16 channels. To perform this, the 8×8 grid GA can be divided into 4×4 sections, for example channels GA1, GA2, GA8, and GA9 can form a new channel group. The user can perform the channel grouping by selecting the desired grid, in this example grid GA, and selecting the desired level of grouping, or zoom level, for example by operating a slider, drop-down menu, or any other suitable manner of making a selection. The user can select from different levels of grouping for each grid, for example 2, 4, 8, 16, 32, or 64 channels per group, or any other suitable number of channels per group. If the user selects a number of channels per group, and then later wants to change the zoom level of one or more groups, the user can select the groups desired and then select the desired zoom level for the desired groups in the manner described above. If the user wants to change the zoom level of one or more groups to match the zoom level of an existing group, the user can select the one or more groups to be changed, and then select the desired group for matching the zoom level. For example, if a user sets grid GA to have 4 channels per group, and then later examines grid GB, instead of repeating the grouping for grid GB, the user can set the level of grouping of grid GB (and any other additional grids or groups) to match the zoom level of grid GA.

Another aspect of the disclosed subject matter relates to an interactive and user-friendly method for creating montages from EEG data. Montages can be considered fixed entities that are created by editing and rearranging channel lists, and the process can be too laborious and time consuming to perform on the fly. In practice, montages can be rarely created, and if so, by an EEG technologist, not the reviewer. In an exemplary embodiment of the disclosed subject matter, interactive montage modification can be relatively quick, intuitive, and user friendly (for example by selecting groups of channels in a schematic display), and the "montages" can be snapshots of a user's current settings and can be saved and shared.

To preserve or emphasize important features that can be registered by individual sensors and can be obscured by a simple averaging process, a composite synthetic signal can be created. The synthetic signal can be depicted in a manner that appears similar to a standard EEG trace, representing information recorded from a defined spatial region covered by a plurality of sensors as if from a single large sensor. However, if the composite trace is derived only by signal averaging and then applying screen-based anti-aliasing filters, much of the information available, for example from new types of intracranial sensors, can be lost. Accordingly, the "zoom" feature can refer not only to the spatial arrangement of channels but also to the temporal and frequency-dependent information available in the raw signals.

High frequency activity can be much more spatially constrained and lower in amplitude than low frequencies, and thus can be much more likely to be obscured by the averaging process as well as by the typical manner in which EEG signals are rendered onto the screen. Typically, signals can be filtered at ⅓ or ¼ the horizontal screen resolution to avoid the appearance of aliasing of higher frequencies, then rendered onto the screen to appear as a continuous bumpy line. This technique can exclude frequencies higher than the filter cutoff, so they can be inaccessible to the reviewer and not available for clinical decision-making. As electrode technology improves, there can be increasing need to include such data in the visual review in a way that is intuitively accessible to the reading physicians or technologists. Therefore, it can be beneficial for high frequencies to be incorporated into the reviewed traces.

Figure 4:
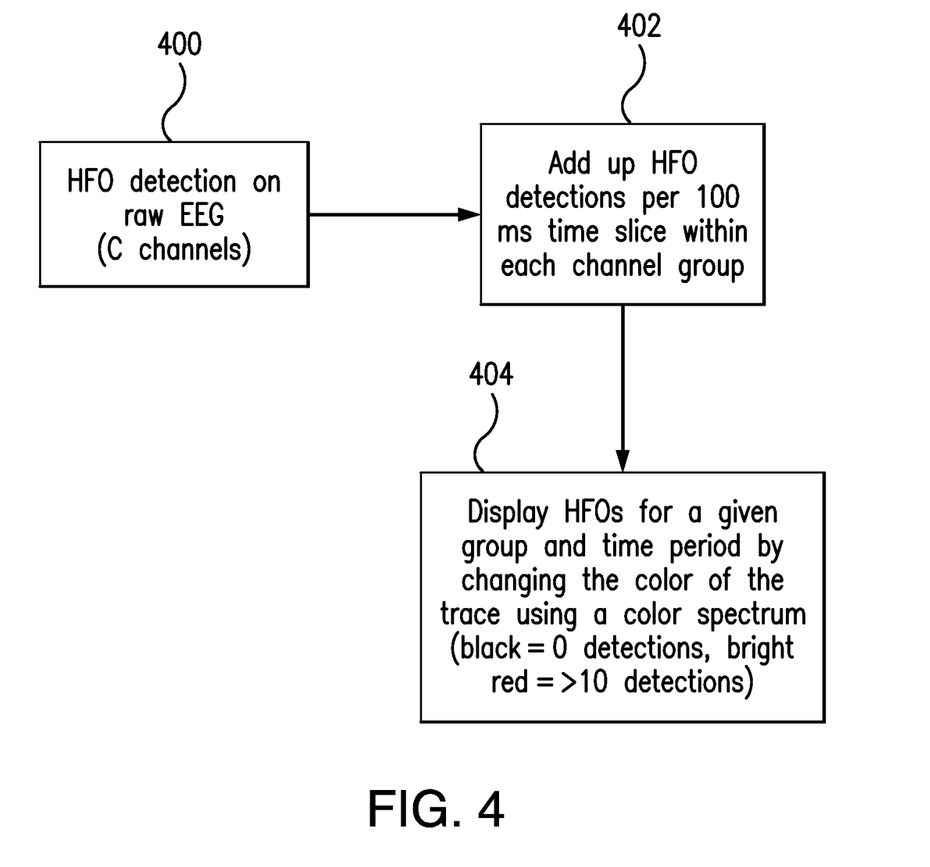
FIG. 4 is a diagram illustrating an exemplary embodiment of the method of FIG. 3.

Referring to FIG. 4 an exemplary arrangement of a feature display of high-frequency oscillations ("HFO") will be described. At 400, HFO detection is performed on the C EEG channels of raw EEG data to detect high-frequency oscillations in the data. At 402, HFO detections are summed for a predetermined time slice, for example a 100 ms time slice, within each channel group. At 404, the HFOs for a given group and time period are displayed, for example by changing the color of the trace using a color spectrum. In an exemplary embodiment, a black color represents zero detections, and a bright red color represents more than ten detections.

In an exemplary embodiment, a composite signal can be formed from averaged low frequencies (for example less than 30 Hz) plus the summed high frequencies. In an alternative embodiment, a signal recorded by each sensor can be filtered into a set of pre-defined frequency bands and then assigned weights directly related to each band that become a multiplier applied to the signal. The resultant weighted signals can then be averaged together to produce the composite trace. To overcome the effects of spatial averaging of high frequencies, a phase shift that is different for each recorded signal can be applied, or the maximum of the amplitude in high frequency bands can be added instead of averaged.

Additionally, specific feature detectors can be used to identify features of particular significance or that might be relatively difficult to recognize visually, because of, for example, brief duration or limited spatial extent. Such features can include microseizures, ripples and fast ripples, which can be limited spatially to <2 mm sq. Detections can be encoded, for example, in the color, thickness or line pattern of the synthetic channel.

Figure 5:
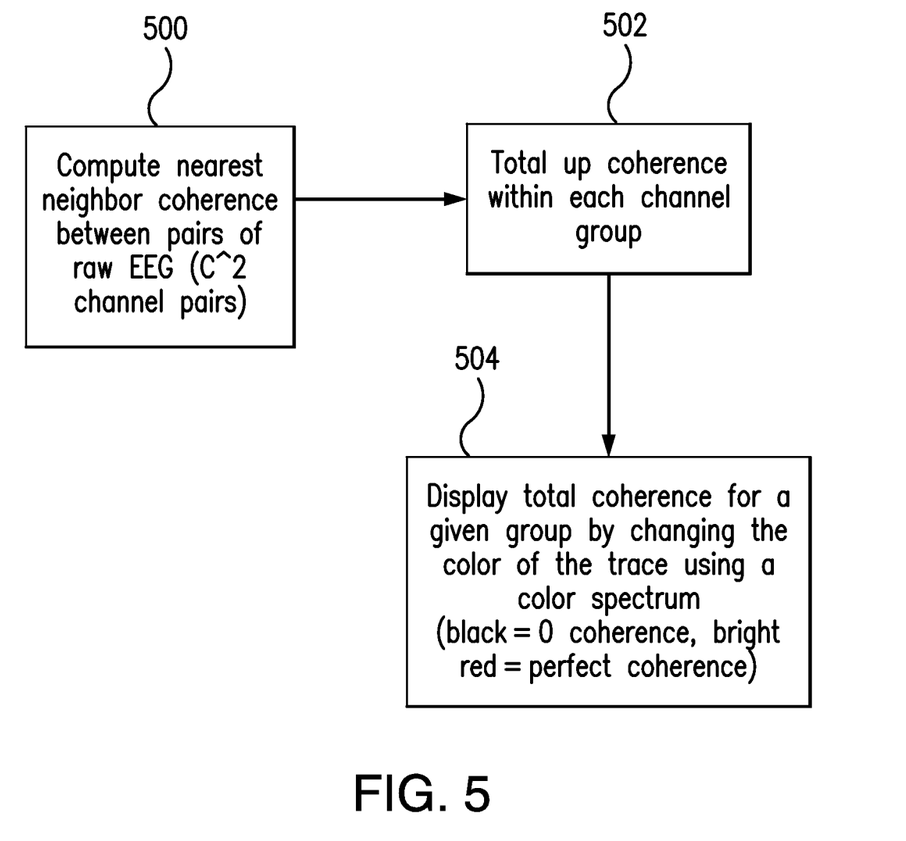
FIG. 5 is a diagram illustrating another exemplary embodiment of the method of FIG. 3.

Referring to FIG. 5, an exemplary arrangement of a feature display of coherence will be described. At 500, coherence is computed between pairs of C EEG channel pairs. For example, coherence can be computed using nearest neighbor computation. At 502, the coherence within each channel group is summed. At 504, the total coherence for a given group is displayed by changing the color of the trace using a color spectrum. In an exemplary embodiment, black represents zero coherence, and bright red represents perfect coherence, for example.

Figure 6A:
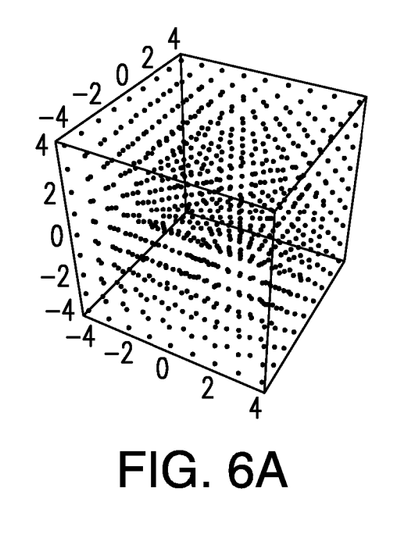
FIGS. 6A-6C are diagrams illustrating further details of the method of FIG. 1.
Figure 6B:
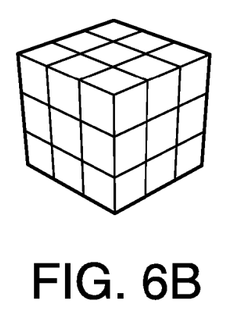
Figure 6C:
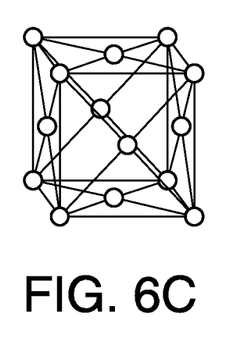

FIGS. 6A-6C illustrate spatial zooming according to the disclosed subject matter. At each point in time, EEG can equal a voltage measured at granularity in 3D space, determined by the sensor density of the acquisition system, as shown for example in FIG. 6A. The zoom process can reduce that granularity by dividing the original lattice cube of voltages into a set or rectangular solids, as shown for example in FIG. 6B, and combining the voltage values (P) in the points within each rectangular solid to produce a single value, thereby producing a smaller lattice cube consisting of these new values (Q), as shown for example in FIG. 6C. This can be represented by the equation $$Q = f(P_{1-x}, P_{1-y}, P_{1-z}) \quad (1)$$

where x, y, and z correspond to the dimensions of the rectangular solid, i.e. the zoom factors in each of the x, y, and z dimensions. In the simple case where zooming simply averages the voltage of all points within each solid, Q can be represented by the equation, $$Q = \frac{\sum_{i=1}^{x} \sum_{j=1}^{y} \sum_{k=1}^{z} P_{i,j,k}}{y * z * x} \quad (2)$$

Figure 7:
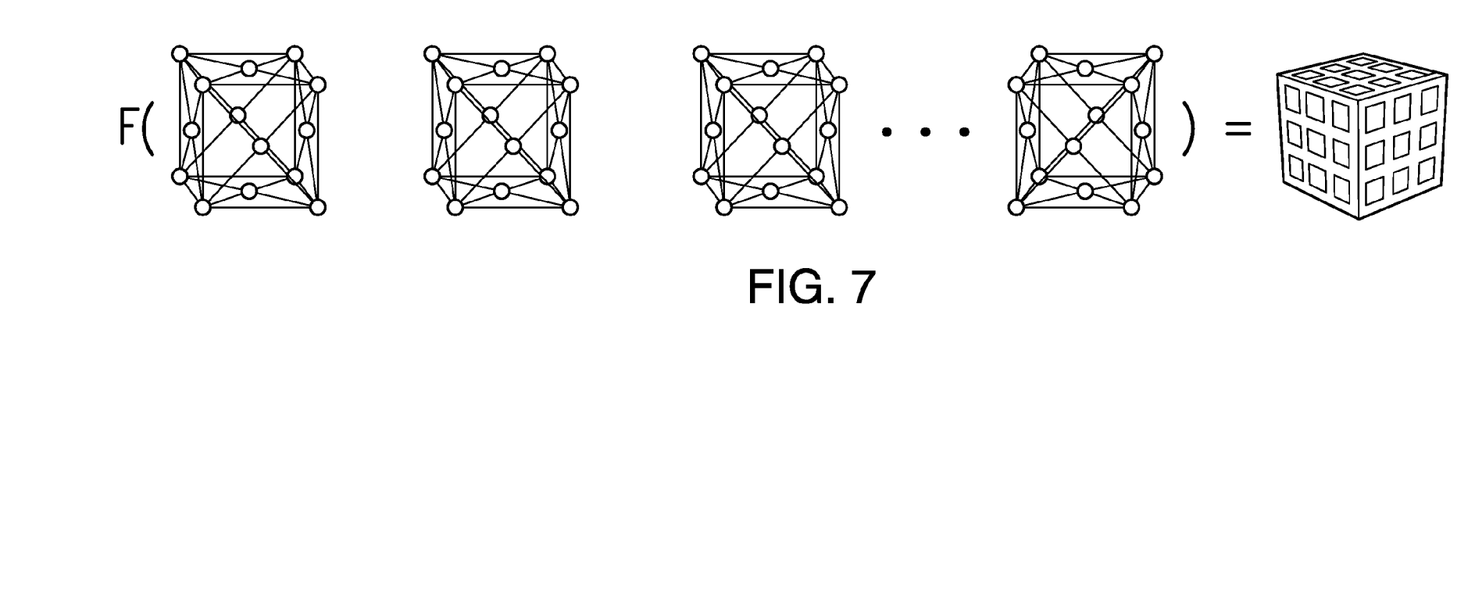
FIG. 7 is a diagram illustrating further details of the method of FIG. 1.

Temporal zooming can operate in a similar manner, combining a number (i.e. the temporal zoom factor) of consecutively sampled lattice cubes Q, to produce a zoomed lattice cube R, as shown for example in FIG. 7. In the simple case, each value in R would simply be the mean of corresponding values in the consecutive sets Q. Alternatively, other combinatorial functions could be applied to the 4 dimensional rectangular solids (i.e. rectangular solids over time) to produce the equation $$Q = f(P_{1-x}, P_{1-y}, P_{1-z}, T_{1-w}) \quad (3)$$

including, but not limited to coherence measures or unit or multiunit activity.

As an example and not by way of limitation, as shown in FIG. 8, the computer system having architecture 800 can provide functionality as a result of processor(s) 801 executing software embodied in one or more tangible, computer-readable media, such as memory 803. The software implementing various embodiments of the present disclosure can be stored in memory 803 and executed by processor(s) 801. A computer-readable medium can include one or more memory devices, according to particular needs. Memory 803 can read the software from one or more other computer-readable media, such as mass storage device(s) 835 or from one or more other sources via communication interface. The software can cause processor(s) 801 to execute particular processes or particular parts of particular processes described herein, including defining data structures stored in memory 803 and modifying such data structures according to the processes defined by the software. An exemplary input device 833 can be, for example, an EEG sensor to provide EEG data to the input interface 823. An exemplary output device 834 can be, for example, a monitor or other suitable device for providing a graphical display of the output from the output interface 824. In addition or as an alternative, the computer system can provide functionality as a result of logic hardwired or otherwise embodied in a circuit, which can operate in place of or together with software to execute particular processes or particular parts of particular processes described herein. Reference to software can encompass logic, and vice versa, where appropriate. Reference to a computer-readable media can encompass a circuit (such as an integrated circuit (IC)) storing software for execution, a circuit embodying logic for execution, or both, where appropriate. The present disclosure encompasses any suitable combination of hardware and software.

While this disclosure has described several exemplary embodiments, there are alterations, permutations, and various substitute equivalents, which fall within the scope of the disclosed subject matter. It should also be noted that there are many alternative ways of implementing the methods and apparatuses of the disclosed subject matter.

The foregoing merely illustrates the principles of the disclosed subject matter. Various modifications and alterations to the described embodiments will be apparent to those skilled in the art in view of the teachings herein. It will be appreciated that those skilled in the art will be able to devise numerous modifications which, although not explicitly described herein, embody its principles and are thus within its spirit and scope.

The invention claimed is:

1. A method for organizing and displaying EEG data obtained from a plurality of EEG channels on a computer system in a user-friendly manner, comprising:
   placing the plurality of EEG channels into a schematic placement diagram;
   dividing the plurality of EEG channels, using a processor configured to receive EEG signals from an EEG sensor array, into a plurality of channel groups, wherein the plurality of channel groups are determined based on the physical layout of the plurality of EEG channels;
   producing a single trace for each channel group using a processor configured to combine two or more of the plurality of EEG channels in the channel group into the single trace;
   for each of the plurality of channel groups, displaying the single trace.

2. The method of claim 1, further comprising selecting a plurality of the plurality of channel groups for zooming out.

3. The method of claim 2, further comprising merging the selected plurality of the plurality of channel groups into a new single trace.

4. The method of claim 1, further comprising selecting one of the plurality of channel groups for zooming in.

5. The method of claim 4, further comprising dividing the selected one channel group into a plurality of composite channels.

6. The method of claim 1, further comprising displaying a montage.

7. The method of claim 1, further comprising saving settings for later use or sharing.

8. The method of claim 1, further comprising computing a specific feature from the plurality of EEG channels.

9. The method of claim 8, further comprising mapping the specific feature to a current set of the plurality of channel groups.

10. The method of claim 9, wherein mapping the specific feature includes summing a number of detections of the specific feature for a predetermined time slice within each of the plurality of channel groups.

11. The method of claim 9, further comprising encoding the feature into an EEG display.

12. The method of claim 11, wherein encoding the feature into the EEG display includes changing a color of an EEG trace using a color spectrum.

13. The method of claim 8, wherein the specific feature is a high-frequency oscillation.

14. The method of claim 8, wherein the specific feature is coherence.

15. A system for organizing and displaying EEG data obtained from a plurality of EEG channels on a computer system in a user-friendly manner, comprising:
    a processor programmed with logic for:
       placing the plurality of EEG channels into a schematic placement diagram;
       dividing the plurality of EEG channels into a plurality of channel groups, wherein the plurality of channel groups are determined based on the physical layout of the plurality of EEG channels;
       producing a single trace for each channel group using a processor configured to combine two or more of the plurality of EEG channels in the channel group into the single trace; and
    for each of the plurality of channel groups, displaying the single trace.

16. The system of claim 15, the processor further programmed with logic for selecting a plurality of the plurality of channel groups for zooming out.

17. The system of claim 16, the processor further programmed with logic for merging the selected plurality of the plurality of channel groups into a new single trace.

18. The system of claim 15, the processor further programmed with logic for selecting one of the plurality of channel groups for zooming in.

19. The system of claim 18, the processor further programmed with logic for dividing the selected one channel group into a plurality of composite channels.

20. The system of claim 15, the processor further programmed with logic for displaying a montage.

21. The system of claim 15, the processor further programmed with logic for saving settings for later use or sharing.

22. The system of claim 15, the processor further programmed with logic for computing a specific feature from the plurality of EEG channels.

23. The system of claim 22, the processor further programmed with logic for mapping the specific feature to a current set of the plurality of channel groups.

24. The system of claim 23, wherein mapping the specific feature includes summing a number of detections of the specific feature for a predetermined time slice within each of the plurality of channel groups.

25. The system of claim 23, the processor further programmed with logic for encoding the feature into an EEG display.

26. The system of claim 25, wherein encoding the feature into the EEG display includes changing a color of an EEG trace using a color spectrum.

27. The system of claim 22, wherein the specific feature is a high-frequency oscillation.

28. The system of claim 22, wherein the specific feature is coherence.

* * * * *